United States Patent
Glover et al.

(10) Patent No.: US 10,507,411 B2
(45) Date of Patent: Dec. 17, 2019

(54) HIGH SOLIDS CONTENT WATER SAMPLING SYSTEM

(71) Applicant: 2134761 ONTARIO LTD., Whitby, ON (CA)

(72) Inventors: James Andrew Glover, Oshawa (CA); Richard Hibbs, Whitby (CA)

(73) Assignee: 2134761 ONTARIO LTD., Whitby, ON (CA)

( * ) Notice: Subject to any disclaimer, the term of this patent is extended or adjusted under 35 U.S.C. 154(b) by 142 days.

(21) Appl. No.: 15/723,707

(22) Filed: Oct. 3, 2017

(65) Prior Publication Data

US 2018/0093204 A1 Apr. 5, 2018

Related U.S. Application Data

(60) Provisional application No. 62/403,445, filed on Oct. 3, 2016.

(51) Int. Cl.
*G01N 1/00* (2006.01)
*G01N 33/00* (2006.01)
(Continued)

(52) U.S. Cl.
CPC ......... *B01D 19/0063* (2013.01); *G01N 15/10* (2013.01); *G01N 33/1853* (2013.01); *G01N 2015/1025* (2013.01)

(58) Field of Classification Search
CPC ...... G01N 30/64; G01N 1/4077; G01N 30/06; G01N 30/36; G01N 33/18; G01N 33/0073;
(Continued)

(56) References Cited

U.S. PATENT DOCUMENTS 4,108,602 A * 8/1978 Hanson .................. G01N 13/00
422/67
4,229,971 A * 10/1980 Ririe, Jr. ................ G01N 30/06
436/161
(Continued)

FOREIGN PATENT DOCUMENTS

CN 201251568 6/2009
DE 4041433 6/1992

OTHER PUBLICATIONS

International Search Report for the corresponding PCT application (PCT/CA2017/051175) dated Jan. 15, 2018.
Written Opinion for PCT/CA2017/051175 dated Jan. 5, 2018.

*Primary Examiner* — Brandi N Hopkins
(74) *Attorney, Agent, or Firm* — Hill & Schumacher

(57) ABSTRACT

A device to extract a near continuous stream of sample water from a high solids content source for the purpose of delivery to a liquid analyzer or sensor for test or measurement. The device includes a source of compressed air and a source of chemical cleaning agent that are used in a coordinated effort to purge and clean the sampling system to ensure the water stream is maintained over long periods of time without significant human intervention. The device includes a valve to allow compressed air to intermittently be sent backwards through the sampling line to purge to drain an inline strainer of solids that have built up since the previous air purge. Downstream of the air valve another valve is used to introduce cleaning chemical into the sampling system to clean residual buildup downstream of the inline strainer. A debubbler unit is placed between the air valve and the cleaning chemical valve to remove air from the sampling system after it was introduced during the air purge event.

11 Claims, 2 Drawing Sheets

1: Inline Tee Strainer
2: Air Purge Control Valve
3: Process Pump
4: Debubbler
5: Chemical Clean Control Valve
6: Liquid Sample Analyzer
7: Water Sample Path
8: Air Storage Tank
9: Air Compressor
10: Chemical Clean Pump
11: Chemical Storage Tank
12: Drain with Siphon Control
13: Microprocessor
14: Communication
15: Booster Pump (optional)
16: Backflow Prevention Valve

(51) Int. Cl.
*G01N 15/10* (2006.01)
*B01D 19/00* (2006.01)
*G01N 33/18* (2006.01)

(58) Field of Classification Search
CPC ...... G01N 1/24; G01N 33/0011; G01N 33/26; G01N 1/2247; B01D 29/356; B01D 29/668; B01D 36/001; B01D 61/14; B01D 1/4077
See application file for complete search history.

(56) References Cited

U.S. PATENT DOCUMENTS

| | | | | |
|---|---|---|---|---|
| 5,734,097 | A * | 3/1998 | Capuano | G01N 30/06 436/39 |
| 9,557,313 | B2 * | 1/2017 | Fougere | C10L 1/003 |
| 2009/0165576 | A1 * | 7/2009 | Shin | B01D 61/145 73/863.23 |
| 2015/0101392 | A1 * | 4/2015 | Foote | G01N 1/24 73/23.2 |

* cited by examiner

| | 15 | 16 | 1 | 2 | 3 | 4 | 5 | 6 | 7 | 8 | 9 | 10 | 11 | 12 |
|---|---|---|---|---|---|---|---|---|---|---|---|---|---|---|
| | Booster Pump (OPTIONAL) | Backflow Prevention Valve | Inline Tee Strainer | Air Purge Control Valve | Process Pump | Debubbler | Chemical Clean Control Valve | Liquid Sample Analyzer | Water Sample Path | Air Storage Tank | Air Compressor | Chemical Clean Pump | Chemical Storage Tank | Drain with Siphon Control |
| *Initial* | Off | Open | Normal | Open | Off | Operational | Open | On-Measure | No Flow | Normal | On If X > Setpoint B but X < Setpoint A, Off if X > Setpoint A | Off | Normal | Operational |
| *Normal Operation* | On-Forward | Open | Normal | Open | On-Forward | Operational | Open | On-Measure | Flow | Normal | On If X > Setpoint B but X < Setpoint A, Off if X > Setpoint A | Off | Normal | Operational |
| *Intake Purge* | Off | Closed | Purge | Closed | Off | Operational | Open | Hold | Air Flow Backwards | Discharge | On If X > Setpoint B but X < Setpoint A, Off if X > Setpoint A | Off | Normal | Operational |
| *Intake Purge - HOLD* | On-Forward | Open | Normal | Open | On-Forward | Operational | Open | Hold | Flow | Recharge | On If X > Setpoint B but X < Setpoint A, Off if X > Setpoint A | Off | Normal | Operational |
| *Cleaning -INJECTION* | Off | Open | Normal | Open | Off | Operational | Closed | Hold | No Flow | Normal | On If X > Setpoint B but X < Setpoint A, Off if X > Setpoint A | ON - Forwards | Drain | Operational |
| *Cleaning - HOLD* | Agitation | Open | Normal | Open | Backwash | Operational | Open | Hold | No Flow | Normal | On If X > Setpoint B but X < Setpoint A, Off if X > Setpoint A | Off | Normal | Operational |
| *Cleaning - RECAPTURE* | Off | Open | Normal | Open | Off | Operational | Closed | Hold | No Flow | Normal | On If X > Setpoint B but X < Setpoint A, Off if X > Setpoint A | On - Backwards | Refill | Operational |

Figure 2

HIGH SOLIDS CONTENT WATER SAMPLING SYSTEM

FIELD

The present disclosure is related to apparatus required to provide a near continuous stream of water to a water quality analyzer. The present disclosure particularly relates to several applications within the water and wastewater treatment industry and industrial process industry that require continuous test and measurement of process liquids.

BACKGROUND

There are many applications in water and wastewater treatment as well as industrial process control that require near continuous measurement of certain water quality parameters or some aspect of the process liquid. In some cases, these test parameters can be measured continuously by submersible probes. However, certain measurement parameters and water quality conditions require water samples to be physically removed from the process for proper measurement to be performed herein referred to as bypass analyzers. Such circumstances that require physical removal of the process water for measurement include: process water that requires dilution in order to put it within measurement range of a particular type of measuring device; a measurement parameter is desired that requires reagents to be added to the process water as part of the measurement method; the process is not physically suitable for installation of the equipment required for a submersible probe sensor; the particular measurement parameter required to be measured benefits from larger form factor equipment that lends itself better to installation outside the process.

All bypass analyzers require some degree of ongoing maintenance in order to prevent buildup and clogging from eventually restricting flow to the analyzer. These restrictions to flow occur in certain types of applications more significantly than others including; applications with process water with high levels of solids; applications with high levels of fats, oils and grease in the process water. Therefore, for analyzers to provide a near real-time measurement of the process water, additional sample transport and conditioning equipment is often required to provide the measuring system to operate for any significant length of time continuously without unacceptable levels of human intervention.

Sampling systems for continuous measurement systems range from simple pumps feeding the sample water to an analyzer to full digestion systems and grinders designed to break down larger particulate matter in the sample water into manageable particle sizes. However, there is a current need in the market for a sampling system for high solids process water that is able to provide a reliable and continuous source of process water to a bypass analyzer without significantly changing the composition of the sample water.

SUMMARY

The system or apparatus disclosed herein uses a coordinated combination of a source of compressed air and cleaning chemicals to maintain sample water flow through from the process to a bypass analyzer.

In particular, a valve is used to purge an inline strainer upstream sending any solids captured since the previous purge to drain. In addition, a cleaning valve is operated to allow cleaning fluid to be pumped downstream to the bypass analyzer to remove any buildup formed since the previous clean.

A debubbler is located between the air purge valve and the cleaning valve to remove air introduced to the sample lines during the air purge event. The debubbler is designed with two ports to allow continuous flow through the debubbler to drain to prevent buildup over time. The debubbler is designed to hold a small volume of fluid, which is constantly exchanged, this allows air to separate from the water sample. Air bubbles are discharged to drain. A pump is used to pump sample fluid from the debubbler to the bypass analyzer between cleaning events.

Thus, the present disclosure provides an apparatus for transporting a near continuous liquid sample from a liquid source to a liquid sample analyzer via liquid sample tubing, comprising an inline tee strainer to remove significant solids from the liquid sample, wherein the tee strainer includes an inlet and a first liquid sample outlet port that allows liquid sample to pass directly from the inline tee strainer inlet to a drain through a drain line, and a second liquid sample outlet port that allows liquid sample that has passed through a mesh screen inside the inline tee strainer to continue on to the liquid sample analyzer. The apparatus includes an air purge control valve used to intermittently introduce a source of compressed air with the purpose of purging solids buildup from the inline tee strainer to drain and a source of compressed air connected to the air purge control valve. The system includes a debubbler unit used to remove the air introduced by the air purge control valve from the liquid sample stream, wherein the debubbler comprises a first outlet port connected to drain to both remove air from the liquid sample and to provide continuous liquid sample flow to drain through drain lines, and a second outlet port that allows the liquid sample to continue to the liquid sample analyzer. The apparatus includes a process pump to pull liquid sample from the second outlet port of the debubbler and send it to the liquid sample analyzer, a chemical clean control valve to intermittently introduce cleaning chemical with the purpose of removing buildup downstream of the debubbler, and a source of cleaning chemical connected to the chemical clean control valve. The system includes liquid sample tubing connecting together the inline tee strainer, the air purge control valve, the debubbler, the process pump, the chemical clean control valve, and the liquid analyzer, such that the liquid sample flows from liquid source to liquid analyzer. The system includes a microprocessor connected to the air purge control valve, process pump and chemical clean control valve with the microprocessor being programmed with instructions for coordinated the operation of the air purge control valve, process pump and chemical clean control valve.

The liquid source may be pressurized such that the liquid source is connected to the inline tee strainer via tubing or piping resulting in continuous flow of liquid sample into the inline tee strainer.

The liquid source may be unpressurized and further comprising a booster pump to connect the liquid source via liquid sample tubing to the inline tee strainer resulting in continuous flow of liquid sample into the inline tee strainer, and the booster pump may be programmed to pump intermittently forwards and then backwards in order to cause agitation in the liquid sample to prevent buildup and flow restriction in the liquid sample tubing. This booster pump is connected to, and under control of the microprocessor.

The apparatus may further comprise a chemical clean pump configured to pump a chemical cleaning fluid from a chemical storage tank into the liquid sample stream such that the chemical cleaning fluid removes buildup from the liquid analyzer and surrounding liquid sample tubing. This chemical clean pump is configured to draw the cleaning chemical back into the chemical storage tank for the purpose of chemical cleaning fluid reuse.

The microprocessor may be programmed to instruct the process pump to pull chemical cleaning fluid back from the liquid analyzer to clean the liquid sample tubing upstream of the chemical clean control valve and downstream of the debubbler.

The apparatus may include a compressor and compressed air storage tank interconnected with the air purge control valve to provide a source or compressed air for the intake purge.

The apparatus may include anti-syphon valves connected to the drain lines from the inline tee strainer, debubbler and liquid analyzer.

The apparatus may include a backflow prevention valve connected to the inlet of the the inline tee strainer to prevent compressed air from going back to the liquid source.

A further understanding of the functional and advantageous aspects of the system disclosed herein can be realized by reference to the following detailed description and drawings.

BRIEF DESCRIPTION OF THE DRAWINGS

The apparatus/system disclosed herein will be more fully understood from the following detailed description thereof taken in connection with the accompanying drawing, which form a part of this application, and in which:

FIG. 2 is a spread sheet identifying all the individual components and the state that those components are in during normal operation, intake purge, cleaning, initial state and their associated states such as intake purge hold, cleaning injection, cleaning hold, and cleaning recapture.

DETAILED DESCRIPTION

Figure 1:
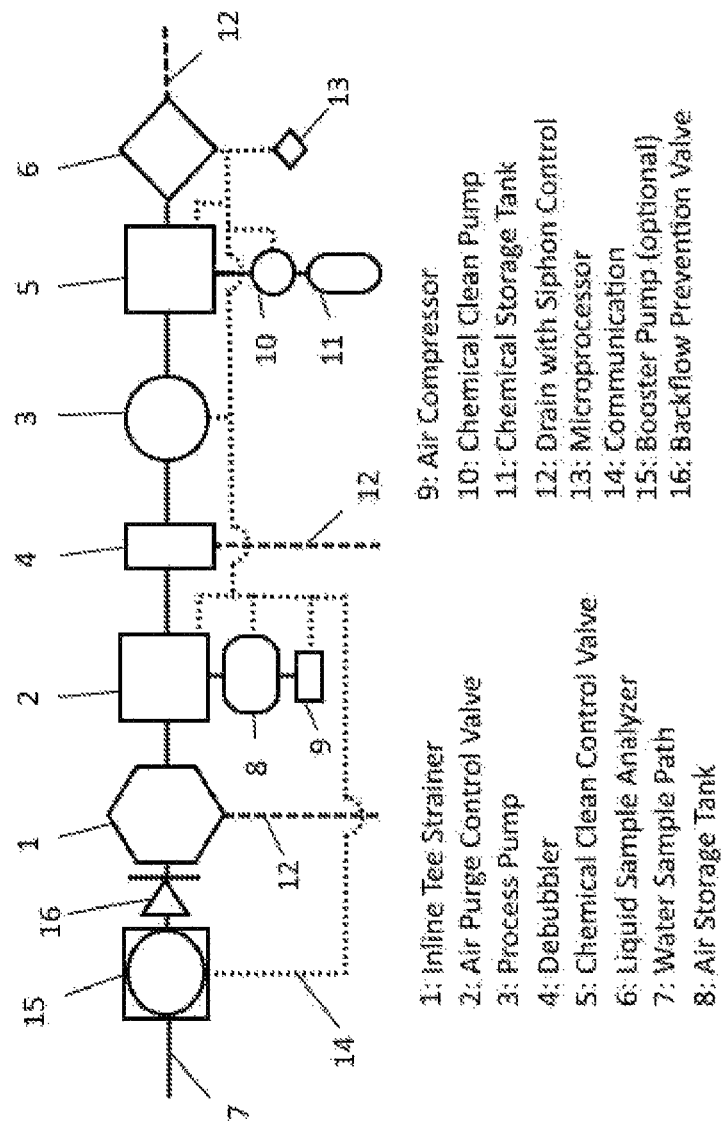
FIG. 1 is a block diagram showing a high solids content water sampling system constructed in accordance with embodiments of the present disclosure.

Various embodiments and aspects of the disclosure will be described with reference to details discussed below. The following description and drawings are illustrative of the disclosure and are not to be construed as limiting the disclosure. The drawings are not to scale. Numerous specific details are described to provide a thorough understanding of various embodiments of the present disclosure. However, in certain instances, well-known or conventional details are not described in order to provide a concise discussion of embodiments of the present disclosure.

As used herein, the terms "comprises" and "comprising" are to be construed as being inclusive and open ended, and not exclusive. Specifically, when used in the specification and claims, the terms "comprises" and "comprising" and variations thereof mean the specified features, steps or components are included. These terms are not to be interpreted to exclude the presence of other features, steps or components.

As used herein, the term "exemplary" means "serving as an example, instance, or illustration," and should not be construed as preferred or advantageous over other configurations disclosed herein.

As used herein, the terms "about" and "approximately" are meant to cover variations that may exist in the upper and lower limits of the ranges of values, such as variations in properties, parameters, and dimensions.

In an embodiment there is provided an apparatus for transporting a near continuous liquid sample from a liquid source to a liquid sample analyzer via liquid sample tubing, comprising an inline tee strainer to remove significant solids from the liquid sample, wherein the tee strainer includes an inlet and a first liquid sample outlet port that allows liquid sample to pass directly from the inline tee strainer inlet to a drain through a drain line, and a second liquid sample outlet port that allows liquid sample that has passed through a mesh screen inside the inline tee strainer to continue on to the liquid sample analyzer. The apparatus includes an air purge control valve used to intermittently introduce a source of compressed air with the purpose of purging solids buildup from the inline tee strainer to drain and a source of compressed air connected to the air purge control valve. The apparatus includes a debubbler unit used to remove the air introduced by the air purge control valve from the liquid sample stream, wherein the debubbler comprises a first outlet port connected to drain to both remove air from the liquid sample and to provide continuous liquid sample flow to drain through drain lines, and a second outlet port that allows the liquid sample to continue to the liquid sample analyzer. The apparatus includes a process pump to pull liquid sample from the second outlet port of the debubbler and send it to the liquid sample analyzer, a chemical clean control valve to intermittently introduce cleaning chemical with the purpose of removing buildup downstream of the debubbler, and a source of cleaning chemical connected to the chemical clean control valve.

The apparatus includes liquid sample tubing connecting together the inline tee strainer, the air purge control valve, the debubbler, the process pump, the chemical clean control valve, and the liquid analyzer, such that the liquid sample flows from liquid source to liquid analyzer. The system includes a microprocessor connected to the air purge control valve, process pump and chemical clean control valve with the microprocessor being programmed with instructions for coordinated the operation of the air purge control valve, process pump and chemical clean control valve.

In an embodiment the liquid source is pressurized such that the liquid source is connected to the inline tee strainer via tubing or piping resulting in continuous flow of liquid sample into the inline tee strainer.

In an embodiment the liquid source is unpressurized and further comprising a booster pump to connect the liquid source via liquid sample tubing to the inline tee strainer resulting in continuous flow of liquid sample into the inline tee strainer.

In an embodiment the booster pump programmed to pump intermittently forwards and then backwards in order to cause agitation in the liquid sample to prevent buildup and flow restriction in the liquid sample tubing.

In an embodiment this booster pump is connected to, and under control of the microprocessor.

In an embodiment the apparatus further comprises a chemical clean pump configured to pump a chemical cleaning fluid from a chemical storage tank into the liquid sample stream such that the chemical cleaning fluid removes buildup from the liquid analyzer and surrounding liquid sample tubing. In an embodiment this chemical clean pump is configured to draw the cleaning chemical back into the chemical storage tank for the purpose of chemical cleaning fluid reuse.

In an embodiment the microprocessor may be programmed to instruct the process pump to pull chemical cleaning fluid back from the liquid analyzer to clean the liquid sample tubing upstream of the chemical clean control valve and downstream of the debubbler.

In an embodiment the apparatus includes a compressor and compressed air storage tank interconnected with the air purge control valve to provide a source or compressed air for the intake purge.

In an embodiment the apparatus includes anti-syphon valves connected to the drain lines from the inline tee strainer, debubbler and liquid analyzer.

In an embodiment he apparatus includes a backflow prevention valve connected to the inlet of the the inline tee strainer to prevent compressed air from going back to the liquid source.

Referring to FIG. 1, a high solids content water sampling system constructed in accordance with the present disclosure is shown.

An inline tee strainer 1 is used to remove solids of significant particle size from the continuous process sample stream. The inline tee strainer 1 includes one inlet port to allow the process sample stream to enter the inline tee strainer 1. The inline tee strainer 1 includes two outlet ports. A first outlet port goes to drain with siphon control 12 where the sample water to drain does not pass through the mesh screen. The second outlet port continues to the air purge control valve 2 and must pass through the mesh screen. The first outlet port acts as a continuous water rinse system for the screen albeit using process water.

The air purge control valve 2 allows the process sample stream to continue to debubbler 4 during normal sampling. During an intake purge event, the valve closes the connection to the debubbler 4 and opens the source of compressed air, air storage tank 8, to the process sample stream. The compressed air goes to the second outlet port of the inline tee strainer 1 and passes backwards through the mesh screen in the inline tee strainer 1 and purges to the first outlet port of the inline tee strainer 1 to drain with siphon control 12. This process purges any buildup in the inline tee strainer 1 that has occurred since the last intake purge event. In the preferred embodiment a backflow prevention valve 16 is used to prevent the compressed air from going back through the booster pump 15 or to the process water source.

The debubbler 4 is used to remove bubbles introduced into the process stream during an intake purge event. The debubbler 4 has one inlet port to allow the process sample stream to enter the debubbler 4. The debubbler 4 has two outlet ports. The first outlet port is located physically at the top of the debubbler 4 unit and is open to drain with siphon control 12 and allows a continuous flow of process sample stream to drain with siphon control 12. The first outlet port purges any air bubbles from the process stream. The second outlet port is located at the bottom of the debubbler 4 unit and allows the process sample stream to proceed to the process pump 3 with air removed. Near continuous flow through the debubbler 4 prevents buildup in the debubbler 4.

The process pump 3 pulls process sample stream from the second outlet port of the debubbler 4. During an intake purge event, the process pump 3 stops pumping. When the air purge control valve 2 closes to the air storage tank 8 the debubbler 4 begins to purge the air from the sampling lines. After a preset time, the debubbler 4 has purged the air and is full of process water at which time the process pump 3 starts pumping the sample water stream to the chemical clean control valve 5.

During normal operation, the chemical clean control valve 5 allows the process sample stream to pass from the process pump 3 to the analyzer 6 for measurement by the analyzer 6. In the preferred embodiment, the process pump 3 supplies a near continuous process sample stream to the analyzer 6. However, those trained in the art will understand that the process pump 3 could be used to pump intermittently in order to supply sample batches to the analyzer 6 instead of a continuous flow.

During a cleaning event, the chemical clean control valve 5 closes the connection to the process pump 3 and the process pump 3 stops pumping. The chemical clean pump 10 then injects a cleaning chemical from the chemical storage tank 11, forward, into the process sample stream to the analyzer 6 where, in the preferred embodiment, the cleaning chemical is held for a preset time for cleaning to take place. Then the chemical clean control valve 5 closes to the chemical clean pump 10. The process pump 3 can then begin pumping the process sample stream, purging the cleaning chemical to drain with siphon control 12, at which time the analyzer 6 may again begin measuring the process sample stream. In a preferred embodiment, the process pump 3 instead pumps backward (backwash) for a preset time to pull the cleaning chemical upstream through the chemical clean control valve 5, through the process pump 3, to the debubbler 4. The process pump 3 then pumps forwards again to send the cleaning chemical back towards the analyzer 6. The cleaning chemical could then be then purged to drain with siphon control 12 through the analyzer 6, but in the preferred embodiment the cleaning chemical is recaptured for later use by opening the chemical clean control valve 5 again and using the chemical clean pump 10 to pull the cleaning fluid back into chemical storage tank 11 for the next clean.

The preferred embodiment uses peristaltic pumps for the process pump 3, chemical clean pump 10 and the booster pump 15 as they operate well in the presence of solids and are easily cleaned and maintained. However, other types of pumps could be used including bellows pumps, syringe pumps, etc.

The preferred embodiment uses a booster pump 15 as an option. This is only necessary when the process source is unpressurized, in which case the booster pump 15 transports the process sample stream from the unpressurized source (tank, open channel, etc.) and sends it through the backflow prevention valve 16 to the inline tee strainer 1.

For a pressurized process source (pressurized pipe, gravity fed source, etc.), the process source is connected to the backflow prevention valve 16. In this case a simple pressure regulator or flow control device should be included before the backflow prevention valve 16.

In the preferred embodiment, the compressed air which is be provided by an air compressor 9 to be stored in the air storage tank 8, or by a secondary compressed air source that must be significantly more than the pressure at the second outlet port of the inline tee strainer 1.

The present system use coordination and control of several electrical components including the air purge control valve 2, chemical clean control valve 5, process pump 3, chemical clean pump 10, air compressor 9 and optional booster pump 15. A microprocessor 13 based control system is programmed to perform a preprogrammed coordinated operation of the system.

Microprocessor 13 is connected to the air purge control valve, process pump and chemical clean control valve, said microprocessor including processing means for coordinated the operation of the air purge control valve 2, process pump 3 and chemical clean control valve 5 and any other microprocessor controllable element, via communication channels 14, which may be hard wired or wireless. In embodiments where a booster pump 15 is utilized, it may be connected to, and under control of said microprocessor 13. Microprocessor 13 is programmed with instructions to coordinate the activity of the above-noted components during the processing. Thus, the present apparatus and method of processing samples may be under computer/microprocessor control.

Some embodiments may be implemented using a processor without additional instructions stored in memory. Some embodiments may be implemented using the instructions stored in memory for execution by one or more general purpose microprocessors. Thus, the disclosure is not limited to a specific configuration of hardware and/or software.

While some embodiments can be implemented in fully functioning computers and computer systems, various embodiments are capable of being distributed as a computing product in a variety of forms and are capable of being applied regardless of the particular type of machine or computer readable media used to actually effect the distribution.

At least some aspects disclosed can be embodied, at least in part, in software. That is, the techniques may be carried out in a computer system or other data processing system in response to its processor, such as a microprocessor, executing sequences of instructions contained in a memory, such as ROM, volatile RAM, non-volatile memory, cache or a remote storage device.

A computer readable storage medium can be used to store software and data which when executed by a data processing system causes the system to perform various methods. The executable software and data may be stored in various places including for example ROM, volatile RAM, nonvolatile memory and/or cache. Portions of this software and/or data may be stored in any one of these storage devices.

Examples of computer-readable storage media include, but are not limited to, recordable and non-recordable type media such as volatile and non-volatile memory devices, read only memory (ROM), random access memory (RAM), flash memory devices, floppy and other removable disks, magnetic disk storage media, optical storage media (e.g., compact discs (CDs), digital versatile disks (DVDs), etc.), among others. The instructions can be embodied in digital and analog communication links for electrical, optical, acoustical or other forms of propagated signals, such as carrier waves, infrared signals, digital signals, and the like. The storage medium may be the internet cloud, or a computer readable storage medium such as a disc.

Furthermore, at least some of the methods described herein are capable of being distributed in a computer program product comprising a computer readable medium that bears computer usable instructions for execution by one or more processors, to perform aspects of the methods described. The medium may be provided in various forms such as, but not limited to, one or more diskettes, compact disks, tapes, chips, USB keys, external hard drives, wire-line transmissions, satellite transmissions, internet transmissions or downloads, magnetic and electronic storage media, digital and analog signals, and the like. The computer useable instructions may also be in various forms, including compiled and non-compiled code.

FIG. 2 is a spread sheet identifying all the individual components and the state that those components are in during normal operation, intake purge, cleaning, initial state and their associated states such as intake purge hold, cleaning injection, cleaning hold, and cleaning recapture.

The foregoing description of the embodiments of the present disclosure have been presented to illustrate the principles of the invention and not to limit the invention to the particular embodiment illustrated. It is intended that the scope of the invention be defined by all of the embodiments encompassed within the following claims and their equivalents.

Therefore what is claimed is:

1. An apparatus for transporting a near continuous liquid sample from a liquid source to a liquid sample analyzer via liquid sample tubing, comprising:
    an inline tee strainer to remove significant solids from the liquid sample, wherein the inline tee strainer includes an inlet and a first liquid sample outlet port that allows liquid sample to pass directly from the inlet of the inline tee strainer to a drain through a drain line, and a second liquid sample outlet port that allows liquid sample that has passed through a mesh screen inside the inline tee strainer to continue on to the liquid sample analyzer;
    an air purge control valve used to intermittently introduce a source of compressed air to purge solids buildup from the inline tee strainer to drain;
    a source of compressed air connected to the air purge control valve;
    a debubbler unit used to remove the air introduced by the air purge control valve from the liquid sample, wherein the debubbler comprises a first outlet port connected to drain and remove air from the liquid sample and to provide continuous liquid sample flow to drain through drain lines, and a second outlet port that allows the liquid sample to continue to the liquid sample analyzer;
    a process pump to pull liquid sample from the second outlet port of the debubbler and send it to the liquid sample analyzer;
    a chemical clean control valve to intermittently introduce cleaning chemical with the purpose of removing buildup downstream of the debubbler;
    a source of cleaning chemical connected to the chemical clean control valve;
    liquid sample tubing connecting together said inline tee strainer, said air purge control valve, said debubbler, said process pump, said chemical clean control valve, and said liquid analyzer, such that the liquid sample flows from liquid source to liquid analyzer; and
    a microprocessor connected to the air purge control valve, process pump and chemical clean control valve, said microprocessor including processing means for coordinating operation of said air purge control valve, process pump and chemical clean control valve.

2. The apparatus according to claim 1 wherein said liquid source is pressurized such that the liquid source is connected to the inline tee strainer via tubing or piping resulting in continuous flow of liquid sample into the inline tee strainer.

3. The apparatus according to claim 1 wherein said liquid source is unpressurized and further comprising a booster pump to connect the liquid source via liquid sample tubing to the inline tee strainer resulting in continuous flow of liquid sample into the inline tee strainer.

4. The apparatus according to claim 3 wherein said booster pump is programmed to pump intermittently forwards and then backwards in order to cause agitation in the liquid sample to prevent buildup and flow restriction in said liquid sample tubing.

5. The apparatus according to claim 4 wherein the booster pump is connected to, and under control of said microprocessor.

6. The apparatus according to claim 1 further comprising a chemical clean pump configured to pump a chemical cleaning fluid from a chemical storage tank into the liquid sample such that said chemical cleaning fluid removes buildup from the liquid analyzer and surrounding liquid sample tubing.

7. The apparatus according to claim 6, wherein the chemical clean pump is configured to draw said cleaning chemical back into said chemical storage tank for the purpose of chemical cleaning fluid reuse.

8. The apparatus according to claim 1, wherein said microprocessor is programmed to instruct said process pump to pull chemical cleaning fluid back from the liquid analyzer to clean the liquid sample tubing upstream of the chemical clean control valve and downstream of the debubbler.

9. The apparatus according to claim 1 wherein the apparatus includes a compressor and compressed air storage tank interconnected with the air purge control valve to provide a source or compressed air for the intake purge.

10. The apparatus according to claim 1 wherein the apparatus includes anti-syphon valves connected to said drain lines from said inline tee strainer, debubbler and liquid analyzer.

11. The apparatus according to claim 1 wherein the apparatus includes a backflow prevention valve connected to the inlet of the said inline tee strainer to prevent compressed air from going back to the liquid source.

\* \* \* \* \*